(12) United States Patent
Addison et al.

(10) Patent No.: US 11,534,112 B2
(45) Date of Patent: Dec. 27, 2022

(54) AI BASED METHOD FOR DETERMINING OXYGEN SATURATION LEVELS

(71) Applicant: Covidien LP, Mansfield, MA (US)

(72) Inventors: Paul S. Addison, Edinburgh (GB); Dean Montgomery, Edinburgh (GB); André Antunes, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 339 days.

(21) Appl. No.: 16/854,177

(22) Filed: Apr. 21, 2020

(65) Prior Publication Data
US 2021/0321951 A1 Oct. 21, 2021

(51) Int. Cl.
| | | |
|---|---|---|
| A61B 5/1455 | (2006.01) | |
| A61B 5/00 | (2006.01) | |
| G16H 50/30 | (2018.01) | |
| G06F 17/14 | (2006.01) | |
| G06F 17/16 | (2006.01) | |
| G06N 3/08 | (2006.01) | |

(52) U.S. Cl.
CPC ........ *A61B 5/7267* (2013.01); *A61B 5/14551* (2013.01); *A61B 5/14552* (2013.01); *A61B 5/726* (2013.01); *A61B 5/7253* (2013.01); *A61B 5/7257* (2013.01); *G06F 17/142* (2013.01); *G06F 17/16* (2013.01); *G06N 3/08* (2013.01); *G16H 50/30* (2018.01)

(58) Field of Classification Search
CPC .............. A61B 5/1455; A61B 5/14551; A61B 5/14552; A61B 5/7267; A61B 5/7253; A61B 5/7257; A61B 5/726
See application file for complete search history.

(56) References Cited

U.S. PATENT DOCUMENTS

| | | | |
|---|---|---|---|
| 7,035,679 B2 * | 4/2006 | Addison | A61B 5/6816 600/323 |
| 2005/0049470 A1 | 3/2005 | Terry | |
| 2011/0276275 A1 | 11/2011 | Addison et al. | |

FOREIGN PATENT DOCUMENTS

WO 20190161411 A1 8/2019

OTHER PUBLICATIONS

International Search Report and Written Opinion issued in PCT Application No. PCT/US21/028091, dated Aug. 18, 2021, 12 pages.
Addison, P.S. (2017). The Illustrated wavelet transform handbook: introductory theory and applications in science, engineering, medicine and finance. CRC press.
Liang, Y., Chen, Z., Ward, R., & Elgendi, M. (2018). Photoplethysmography and deep learning: enhancing hypertension risk stratification. Biosensors, 8(4), 101.

* cited by examiner

*Primary Examiner* — Eric F Winakur
(74) *Attorney, Agent, or Firm* — Holzer Patel Drennan (57) ABSTRACT

Implementations described herein disclose an artificial intelligence (AI) based method for generating an oxygen saturation level output signal using the trained neural network. In one implementation, the method includes receiving a photoplethysmographic (PPG) signal, the PPG signal including a red PPG signal and an infrared PPG signal, generating an input feature matrix by performing time-frequency transform of the PPG signal, training a neural network using the input feature matrix and an oxygen saturation level input signal, and generating an oxygen saturation level output signal using the trained neural network.

19 Claims, 11 Drawing Sheets

AI BASED METHOD FOR DETERMINING OXYGEN SATURATION LEVELS

BACKGROUND

Oximetry is an optical method for measuring oxygenated hemoglobin in blood. Oximetry is based on the ability of different forms of hemoglobin to absorb light of different wavelengths. Oxygenated hemoglobin ($HbO_2$) maximum absorption occurs in the red wavelength and deoxygenated or reduced hemoglobin (RHb) maximum absorption occurs in the near-infrared wavelengths. When red and infrared light are passed through a blood vessel the transmission of each wavelength is inversely proportional to the concentration of $HbO_2$ and RHb in the blood. Pulse oximeters can differentiate the alternating light input from arterial pulsing from the constant level contribution of the veins and other non-pulsatile elements. Generally, only the alternating light input is selected for analysis. Pulse oximetry has been shown to be a highly accurate technique. Pulse oximeters typically provide arterial oxygen saturation, heart rate, and photoplethysmographic (PPG) signals such as a red signal and an infrared signal.

SUMMARY

Implementations described herein disclose an artificial intelligence (AI) based method for generating an oxygen saturation level output signal using the trained neural network. In one implementation, the method includes receiving a photoplethysmographic (PPG) signal, including a red PPG signal and an infrared PPG signal, generating an input feature matrix or matrices by performing time-frequency transform of the PPG signal, training a neural network using the input feature matrices and an oxygen saturation level input signal, and generating an oxygen saturation level output signal using the trained neural network.

A method, of determining oxygen level saturation includes receiving a photoplethysmographic (PPG) signal, the PPG signal including a red PPG signal and an infrared PPG signal, generating an input feature matrix by performing time-frequency transform of the PPG signal, training a neural network using the input feature matrix and an oxygen saturation level input signal, and generating an oxygen saturation level output signal using the trained neural network. In one implementation, generating an input feature matrix by performing time-frequency transform of the PPG signal further includes generating an input feature matrix by performing a wavelet transform of the PPG signal.

In one implementation, generating the input feature matrix by performing time-frequency transform of the PPG signal further comprising generating a modulus value vector and a phase value vector across a time-frequency plane. Alternatively, generating an input feature matrix by performing time-frequency transform of the PPG signal further comprising generating a real value vector and an imaginary value vector across a time-frequency plane. Yet alternatively, generating the input feature matrix by performing a wavelet transform of the PPG signal further comprising generating the input feature matrix by performing a Morlet wavelet transform of the PPG signal.

In one implementation, the method further includes normalizing the PPG signal by a baseline to generate a normalized PPG signal, wherein generating an input feature matrix further comprises generating an input feature matrix by performing time-frequency transform of the normalized PPG signal. Alternatively, the method further includes rescaling the input feature matrix non-linearly before training a neural network using the input feature matrix. Yet alternatively, rescaling the input feature matrix non-linearly further comprising rescaling the input feature matrix using a logarithmic scaling. Alternatively, performing time-frequency transform of the PPG signal further comprising one of performing short time Fourier transform (STFT) of the PPG signal, performing WignerVille transform of the PPG signal, and performing S-transform of the PPG signal. Alternatively, the method further includes combining two or more vectors of the input feature matrix to generate a combined feature vector and wherein training the neural network further comprising training the neural network with the combined feature vector.

In a computing environment, a method performed at least in part on at least one processor, the method including receiving a photoplethysmographic (PPG) signal, the PPG signal including a red PPG signal and an infrared PPG signal, generating an input feature matrix by performing time-frequency transform of the PPG signal, training a neural network using the input feature matrix and an oxygen saturation level input signal, and generating an oxygen saturation level output signal using the trained neural network.

A physical article of manufacture including one or more tangible computer-readable storage media, encoding computer-executable instructions for executing on a computer system a computer process to provide an automated connection to a collaboration event for a computing device, the computer process including receiving a photoplethysmographic (PPG) signal, the PPG signal including a red PPG signal and an infrared PPG signal, generating an input feature matrix by performing time-frequency transform of the PPG signal, and training a neural network using the input feature matrix and an oxygen saturation level input signal.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Other implementations are also described and recited herein.

BRIEF DESCRIPTIONS OF THE DRAWINGS

A further understanding of the nature and advantages of the present technology may be realized by reference to the figures, which are described in the remaining portion of the specification.

DETAILED DESCRIPTIONS

Hypoxemia is a condition that indicates lower than normal concentration of oxygen levels in arterial blood of a patient. Hypoxemia may result in hypoxia or hypoxic condition for the patient, characterized by inadequate oxygen content in patient tissues. Pulse oximeters may be used to measure the oxygen content of arterial blood to indicate existing hypoxia condition as well as to predict impending hypoxia. Pulse oximeters generate various output signals including fluctuating time series indicating pulse oximeter trace or red and infrared photoplethysmographic (PPG) signals. The red an infrared PPG signals may be processed to generate oxygen saturation levels, also referred to as $SpO_2$ values.

Using deep learning for time series analysis such as the determination of an $SpO_2$ value from the red and infrared PPG signals may involve simply inputting the raw PPG into a network, such as a long-short term memory (LSTM) network or a convolutional neural network (CNN). However, improved results can be obtained by preprocessing the data to provide input features that more succinctly capture the information from the PPG signals. An AI based method for determining oxygen saturation levels disclosed herein includes time-frequency processing of the red and infrared PPG signals to generate an input feature matrix that are then input into a machine learning model such as a deep learning AI model based on CNNs.

Figure 1:
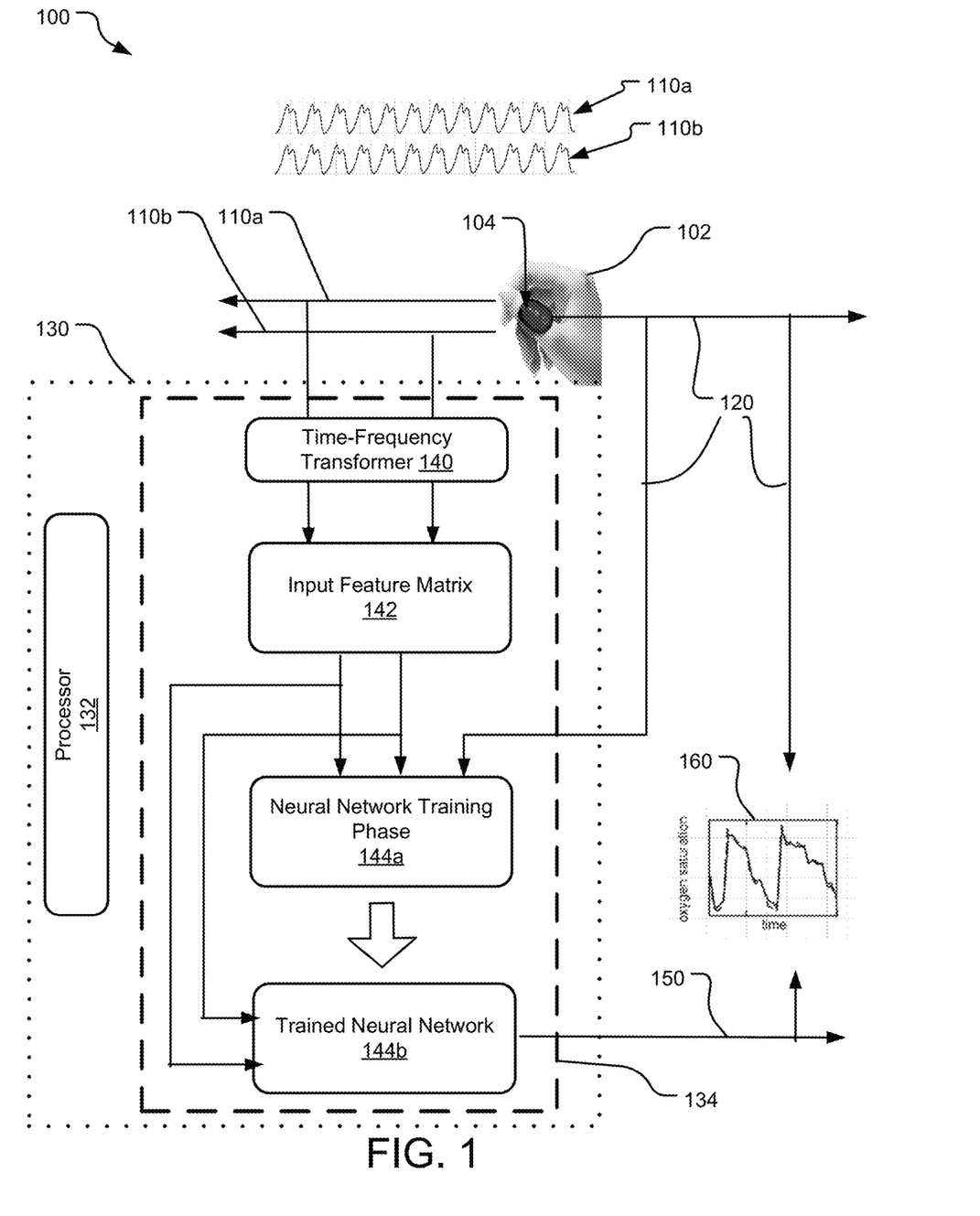
FIG. 1 illustrates an example schematic view of an AI based system for determining oxygen desaturation levels using time-frequency preprocessing for the determination of input features.

FIG. 1 illustrates an example schematic view of an AI based system 100 for determining oxygen desaturation levels using time-frequency preprocessing for the determination of input features. An oximeter 104 may be used to measure the oxygen saturation ($SpO_2$) level in the patient. For example, the pulse oximeter 104 may be attached to the patient's thumb. The pulse oximeter 104 may be communicatively connected to a computing system 130. For example, the pulse oximeter 104 may be connected to the computing system 130 wirelessly and it may send a sequence of input signals 110 measured by the oximeter 104 over a period of time. For example, such input signal sequence 110 may be communicated at every second. In one implementation, the input signal sequence 110 may include PPG signals such as a red signal 110a, an infrared signal 110b, etc. The pulse oximeter 104 may also use the values of the red signal 110a and the infrared signal 110b, to generate values of oxygen saturation levels (the $SpO_4$ levels). A sequence of such $SpO_4$ levels generated by the pulse oximeter 104 is illustrated by a sequence of oxygen saturation levels 120 (or a sequence of $SpO_4$ levels 120).

The computing system 130 may be a computing system that includes a microprocessor 132 and various other components implemented on a memory 134. An example of such a computing system 130 is disclosed in FIG. 10 below. In a method disclosed herein, the memory 134 may be used to store the sequence of input signals 110 generated by the pulse oximeter 104, the sequence of $SpO_4$ levels 120 generated by the pulse oximeter 104, as well as an input feature matrix or matrices 142 generated based on the sequence of input signals 110. The combination of the input matrices 142 may also be referred as tensors. For example, a time-frequency transformer 140 may be used to generate the input feature matrix 142 based on the sequence of input signals 110.

In one implementation, the time-frequency transformer 140 may be a wavelet transformer that allows a signal to be decomposed such that both the frequency characteristics and the location of particular features in a time series may be highlighted simultaneously. The nature of the wavelet transform is such that it is well suited to the analysis of signals in which a more precise time resolution is required for higher frequencies than for lower ones, such as PPG signals. Furthermore, by employing a variable width window, it effectively zooms in on the temporal signal when analyzing higher frequencies, thus providing higher temporal resolution where necessary. In one implementation, the wavelet transform of a continuous real-valued time signal, x(t), with respect to the wavelet function, w is defined as:

$$T(a, b) = \frac{1}{\sqrt{a}} \int_{-\infty}^{\infty} \psi^*\left(\frac{t-b}{a}\right) x(t) dt$$

Where t is time, a is the dilation parameter, b is the location parameter, ψ((t-b)/a) is the analyzing wavelet used in the convolution and, ψ*((t-b)/a) is its complex conjugate, and x(t) is the signal under investigation which, in this application, may be the PPG signals 110 obtained from the pulse oximeter 104. Examples of various wavelets that may be used by the time-frequency transformer 140 may include a Morlet wavelet, a Mexican hat wavelet, a Paul Wavelet, etc. Alternatively, discrete wavelet transforms with corresponding discrete wavelets may also be used. In other implementations, variants of the same wavelet, such as a Morlet wavelet having different characteristic (or central) frequencies, may also be used.

In one example implementation using Morlet wavelet at the time-frequency transformer 140, the central frequency Wo, is set to 5.5. However, alternative central frequencies, such as values less than 5.5 (e.g. 2.5 or 1.5), which are better at extracting temporal information may also be used. Alternatively, in other implementations, values greater than 5.5 (e.g. 10, 15), which are better at extracting low frequency measures from the signal may be used as the central frequency. In another implementation, the time-frequency transformer 140 may run continuous wavelet transform on the input signal 110 using a Morlet wavelet set at two, or more, separate values of the wavelet central frequencies (coo) and input the modulus and phase from these additional matrices as additional inputs into the neural network training phase 144a.

The output of the time-frequency transformer 140 may be stored as an input feature matrix 142. The input feature matrix 142 may be a matrix of complex number values in a time frequency plane. An example of such a matrix may be a matrix of modulus values across the time-frequency plane. Another such example may be a matrix of phase values across the time-frequency plane. Such modulus and phase values across time-frequency plane are illustrated below in FIG. 2.

In an alternative implementation, the time-frequency transformer 140 may normalize the PPG signal 110 by its baseline before computing the wavelet transform. Alternatively, the transform values output from the time-frequency transformer 140 may be rescaled in a nonlinear way in order to enhance the subtle features within the signal. For example, the modulus values output from the time-frequency transformer 140 may be logarithmically scaled and the scaled values may be used as part of the input feature matrix 142.

Implementations of the time-frequency transformer 140 may use alternate transforms such as short time Fourier transform (STFT), Wigner-Ville transform, S-transform, etc. Alternatively, such alternative transforms may be computed and combined with a wavelet transform or with each other and the combination transform may be input to the neural network training phase 144a. Similarly, different time-frequency transforms may be used as additional inputs to the neural network training phase 144a. For example, the phase and modulus matrix from a wavelet transform plus a phase and modulus matrix from a short time Fourier transform may be used as inputs to the neural network training phase 144a. Alternatively, only part of such transform, e.g. the real part, imaginary part, modulus, or phase may be used at input to the neural network training phase 144a.

The input feature matrix 142 and the sequence of oxygen saturation levels 120 generated by the pulse oximeter 104 are used as inputs to train a new neural network at a neural network training phase 144a. For example, the neural network may be a deep learning network such as a CNN.

Once the neural network is trained, as indicated by the trained neural network 144b, the input feature matrix 142 may be input to the trained neural network 144b to generate a predicted oxygen saturation level sequence 150. A comparison of the predicted oxygen saturation level sequence 150 and the sequence of oxygen saturation levels 120 generated by the pulse oximeter 104 is depicted at 160 (and further illustrated below in FIG. 5).

In one implementation, various vectors of the input feature matrix 142 may be combined in some way before being input into the deep learning neural network 144a. For example, the modulus values of the red signal wavelet transform may be divided by the modulus values of the infrared signal wavelet transform. Subsequently, this ratio transform may be used as input to the deep learning neural network 144a. Other operations apart from division may also be employed.

Figure 2:
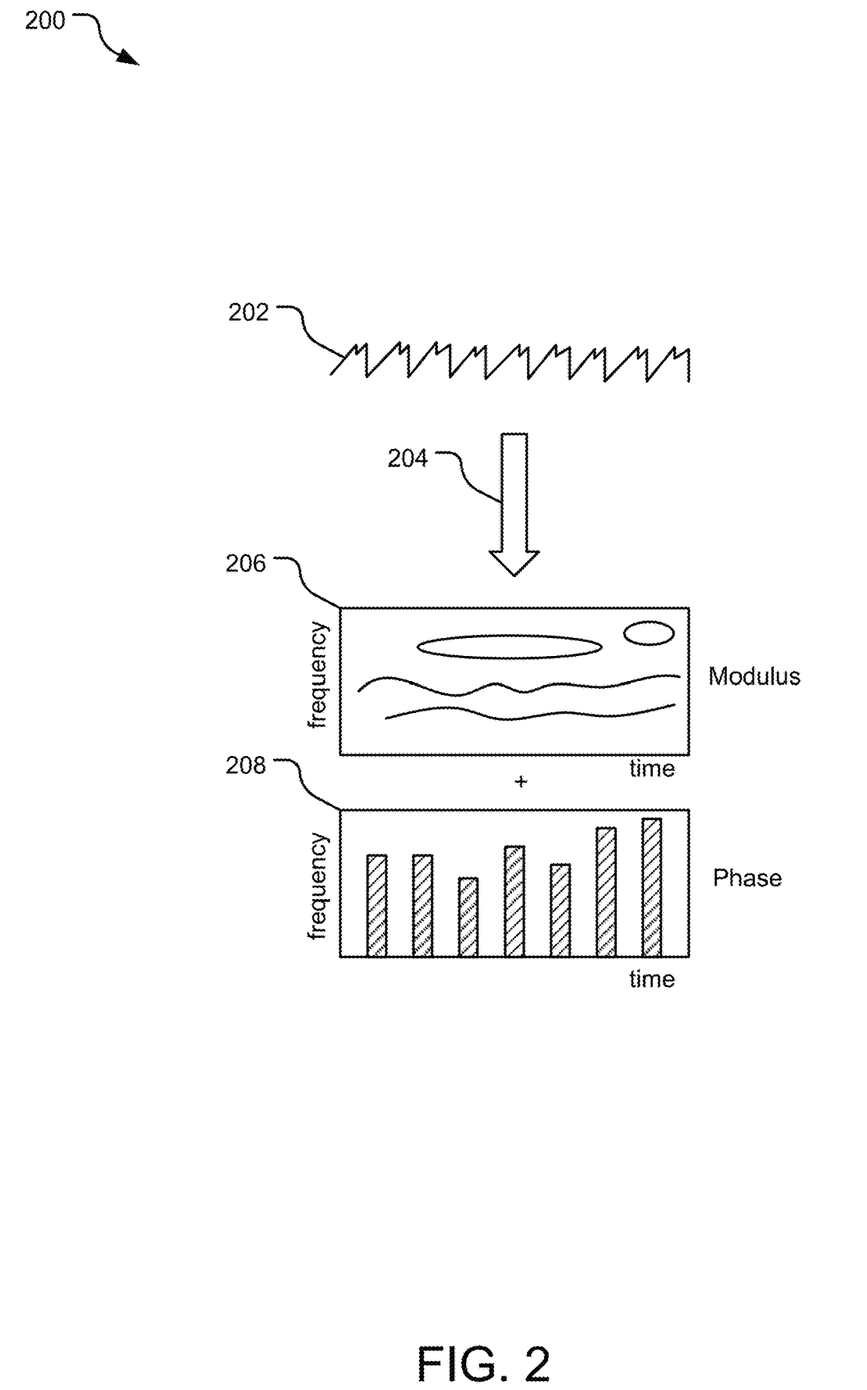
FIG. 2 illustrates example schematic 200 of the wavelet transform process to generate the input feature matrix.

FIG. 2 illustrates example schematic 200 of the wavelet transform process to generate the input feature matrix. Specifically, the schematic 200 illustrates an input PPG signal 202 is transformed at 204 to generate a modulus matrix 206 in a time-frequency plane and a phase matrix 208 in a time-frequency plane.

Figure 3:
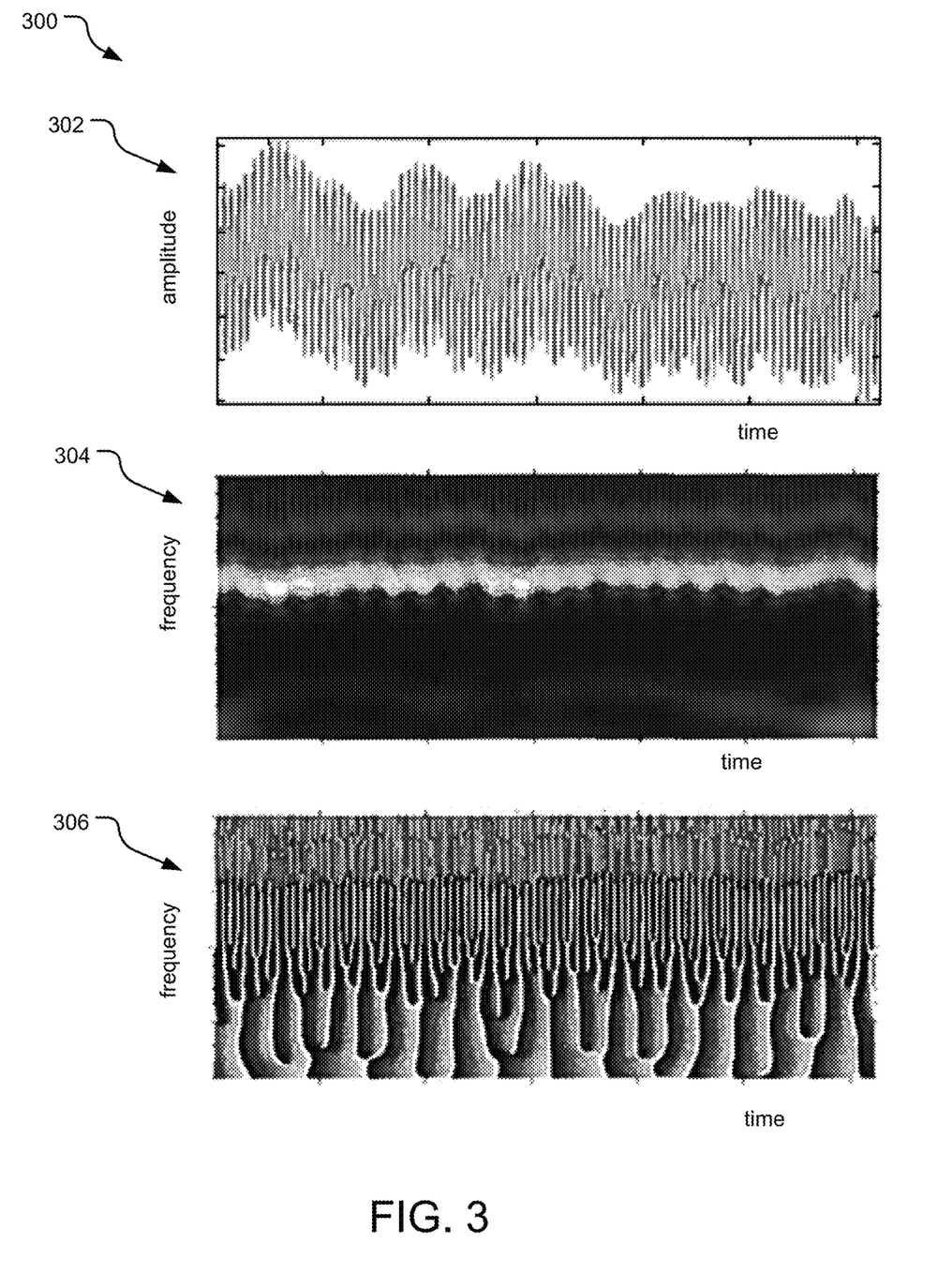
FIG. 3 illustrates example depictions of the wavelet transform modulus and phase maps derived from a PPG.

FIG. 3 illustrates example depictions 300 of the wavelet transform modulus map 304 and a phase map 306 derived from a PPG signal 302. The matrix representing the modulus map 304 and a phase map 306 may be input to a deep learning network such as a CNN in order to derive oxygen saturation levels.

Figure 4:
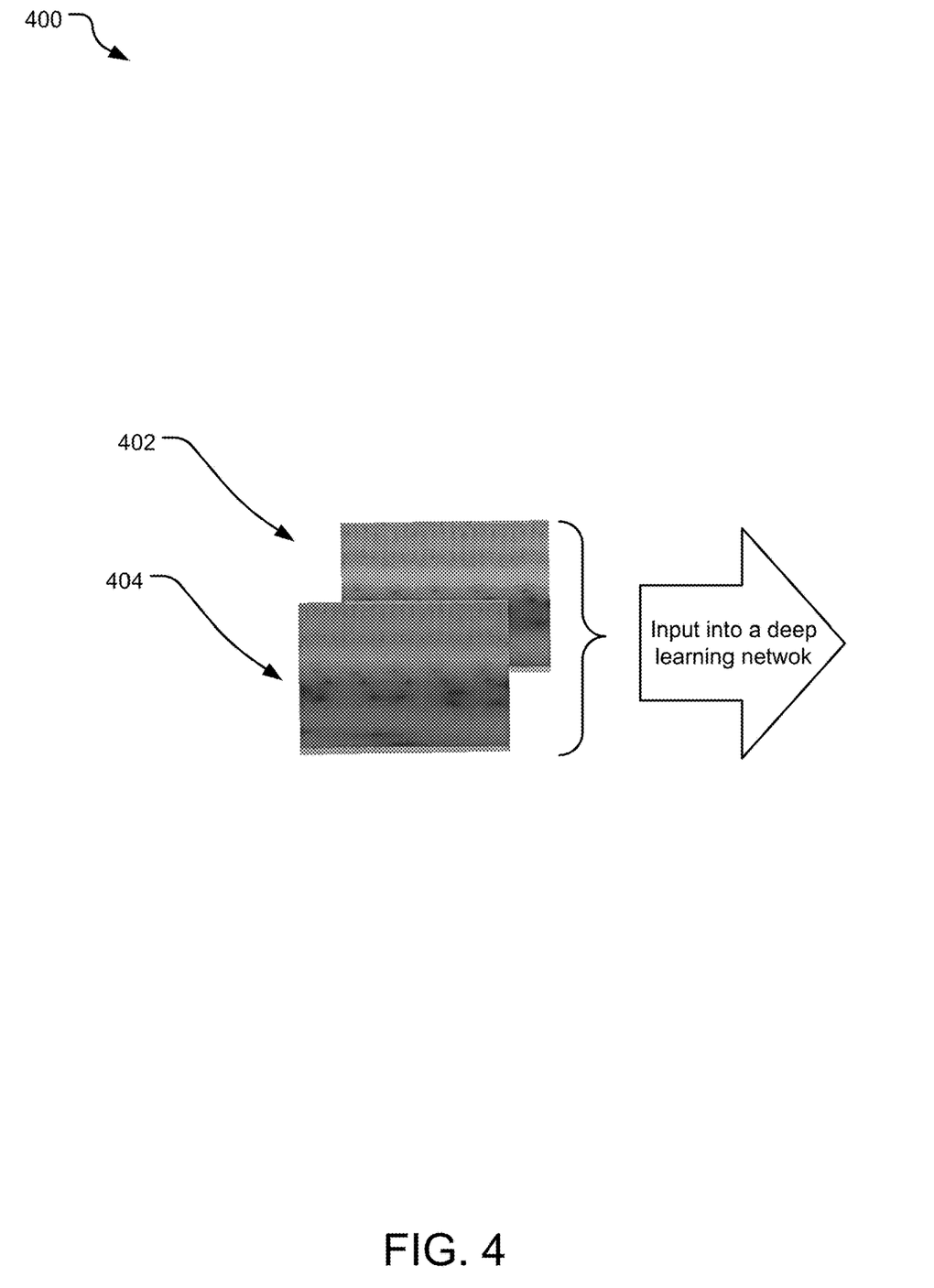
FIG. 4 illustrates an example a schematic of the modulus matrices of the red and infrared PPG signals being input to a deep learning model.

FIG. 4 illustrates an example a schematic of the modulus matrices 400 of the red and infrared PPG signals being input to a deep learning model. Specifically, a modulus matrix 402 is generated by time-frequency transform of red PPG signal and a modulus matrix 404 is generated by time-frequency transform of infrared PPG signal. Both of these matrices are input to a deep learning network.

Figure 5:
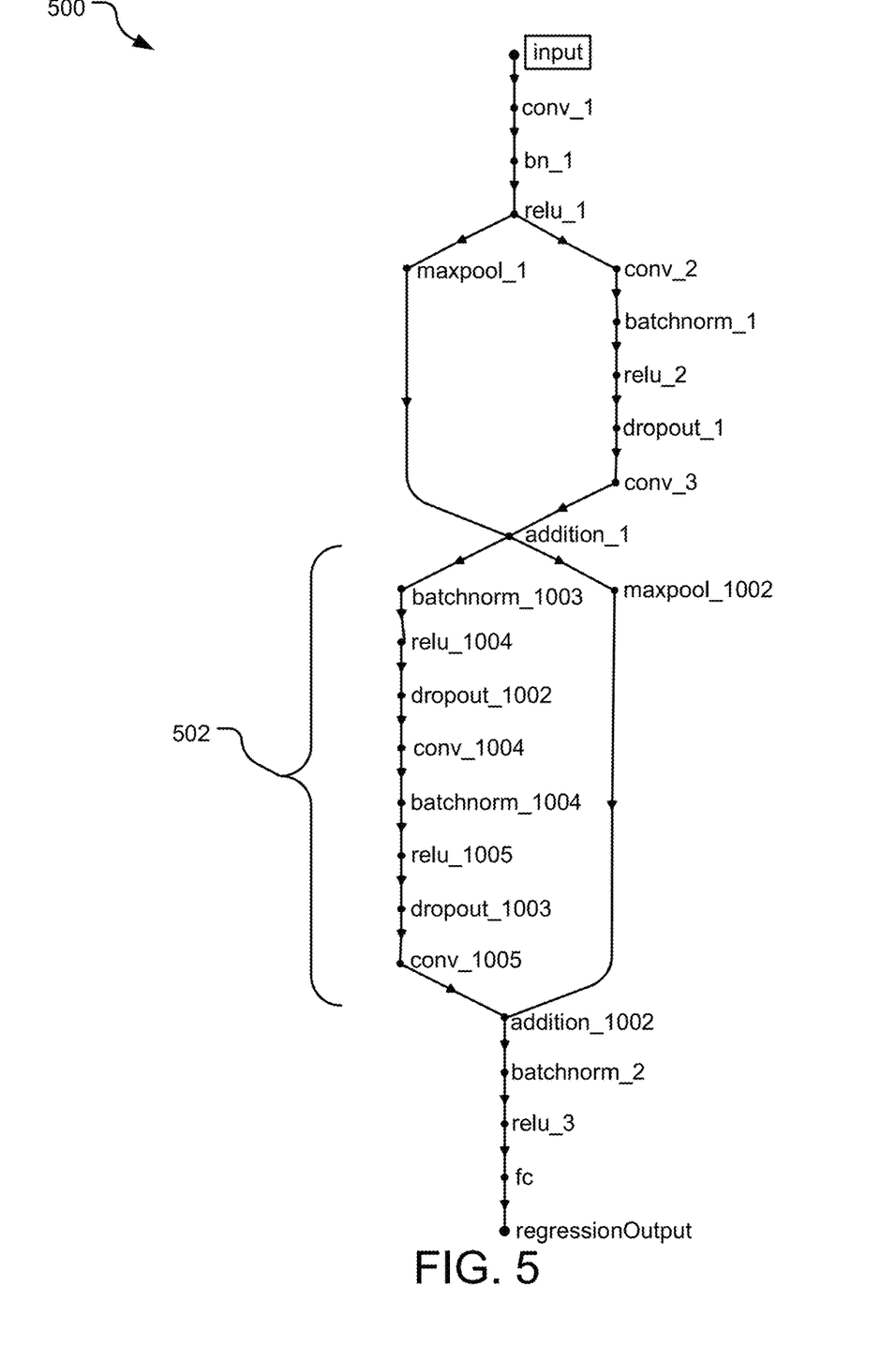
FIG. 5 illustrates an example implementation of a deep learning network.

FIG. 5 illustrates an example implementation of a deep learning network 500. The illustrated deep learning network 500 is a convolutional neural network (CNN). Here a series of blocks 502 which may be repeated an arbitrary number of times.

Figure 6:
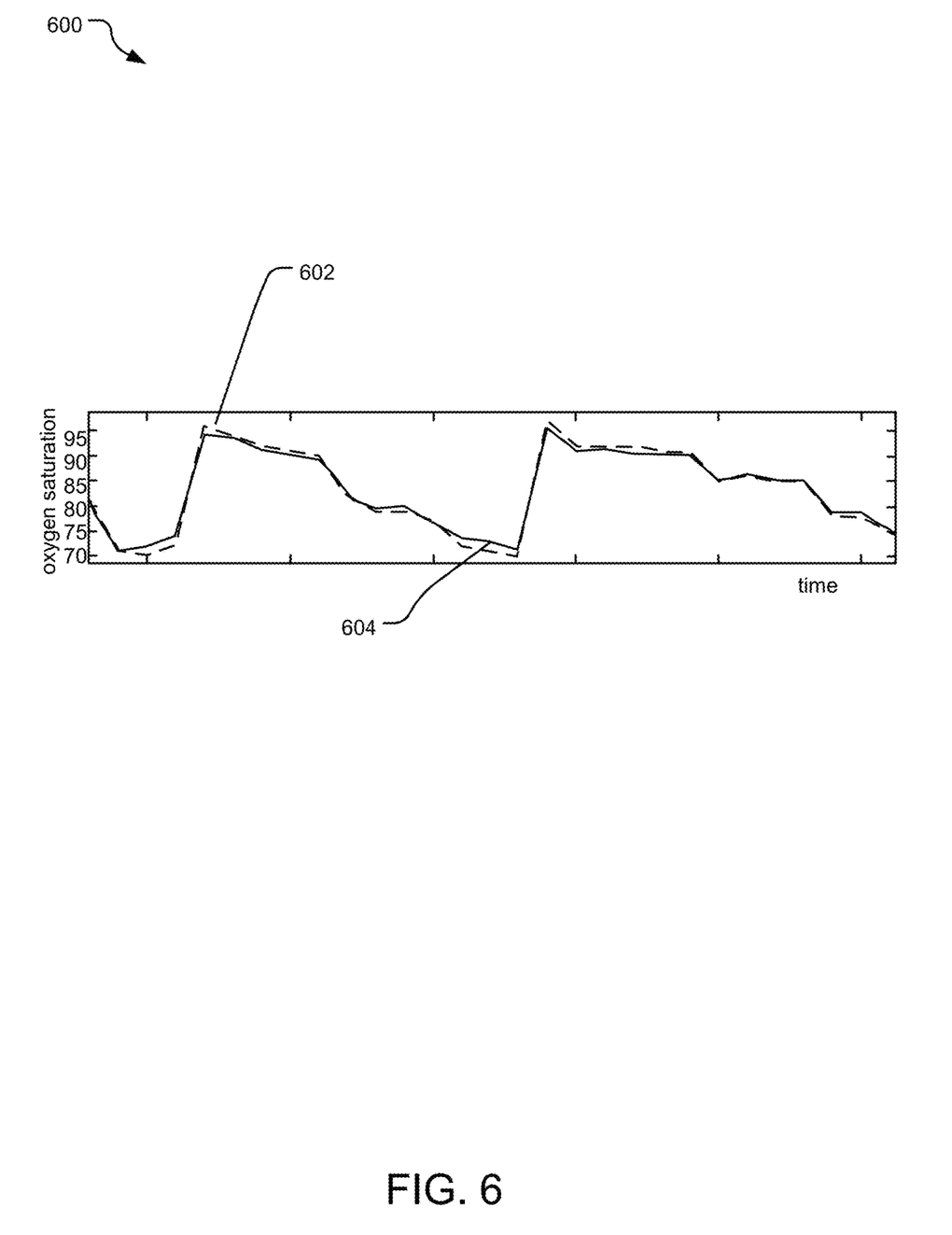
FIG. 6 illustrates example output of the deep leaning model compared to the true oxygen saturation levels.

FIG. 6 illustrates example comparative graph 600 of the output of the deep learning model compared to the true oxygen saturation levels using the input from the modulus matrices from the red and infrared signals described in FIG. 4. Specifically, FIG. 6 illustrates sequential desaturation events over a period of time. As illustrated herein, the dashed line 602 is the oxygen saturation level truth and the solid line 604 is the predicted oxygen saturation level derived from the deep learning model.

Figure 7:
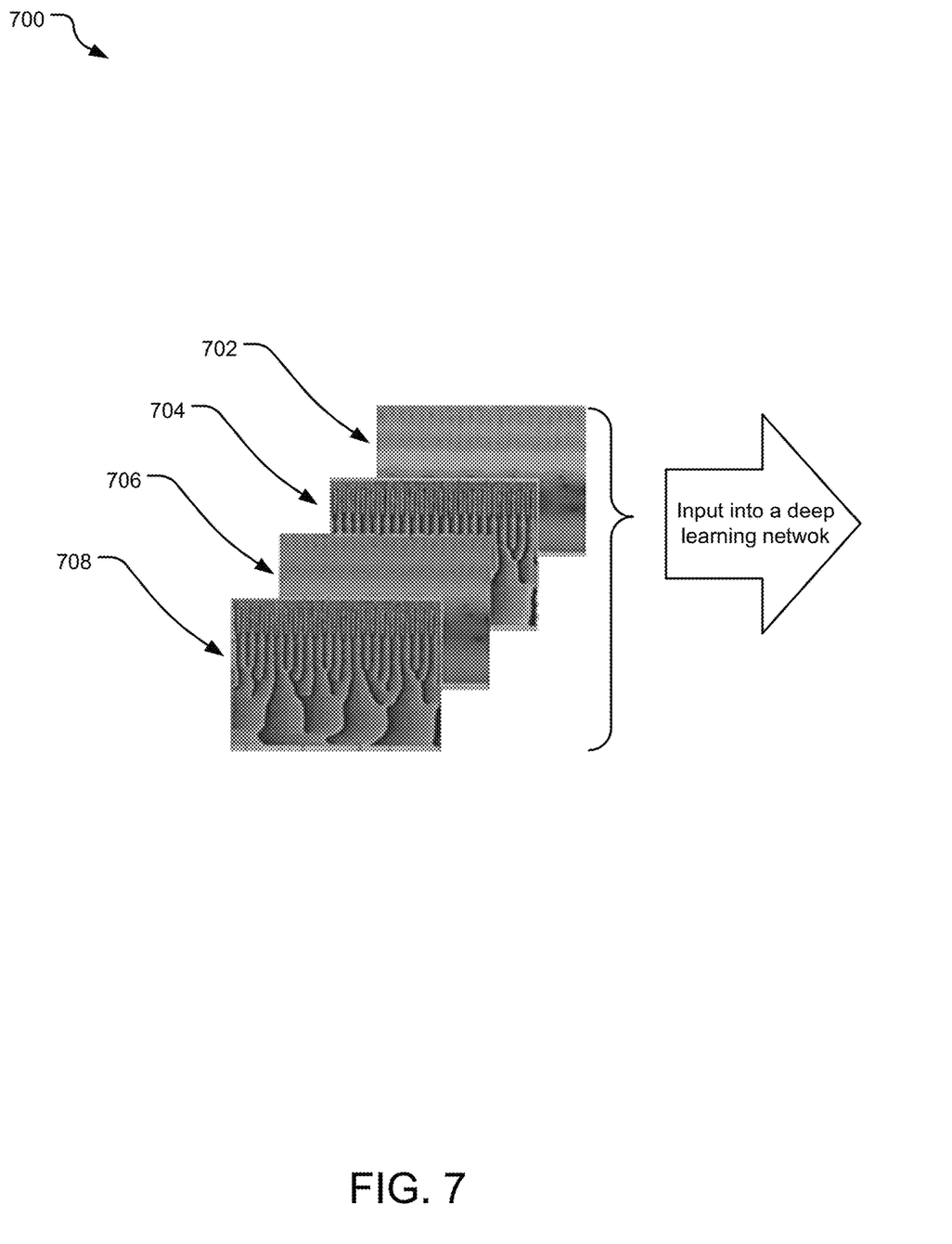
FIG. 7 illustrates an alternative example schematic of another example input to the deep learning model where both the red and infrared signal modulus and phase are input to the network.

FIG. 7 illustrates an alternative example schematic of another example input to the deep learning model where both the red and infrared signal modulus and phase are input to the network. Specifically, a modulus matrix 702 is generated by time-frequency transform of red PPG signal and a modulus matrix 706 is generated by time-frequency transform of infrared PPG signal. Furthermore, a phase matrix 704 is generated by time-frequency transform of red PPG signal and a phase matrix 708 is generated by time-frequency transform of infrared PPG signal. Each of these four matrices are input to a deep learning network. In alternative implementations, the modulus matrices and the phase matrices from a number of wavelet transforms may be used for red and infrared signals. For example, an implementation may use a number of Morlet wavelet transforms of each signal where the characteristic frequency of the Morlet analyzing wavelet is changed for each transform. For example, if three characteristic frequencies are used, three modulus and three phase matrices per signal, thus a total of twelve matrices, may be generated and used as input to the training network.

Figure 8:
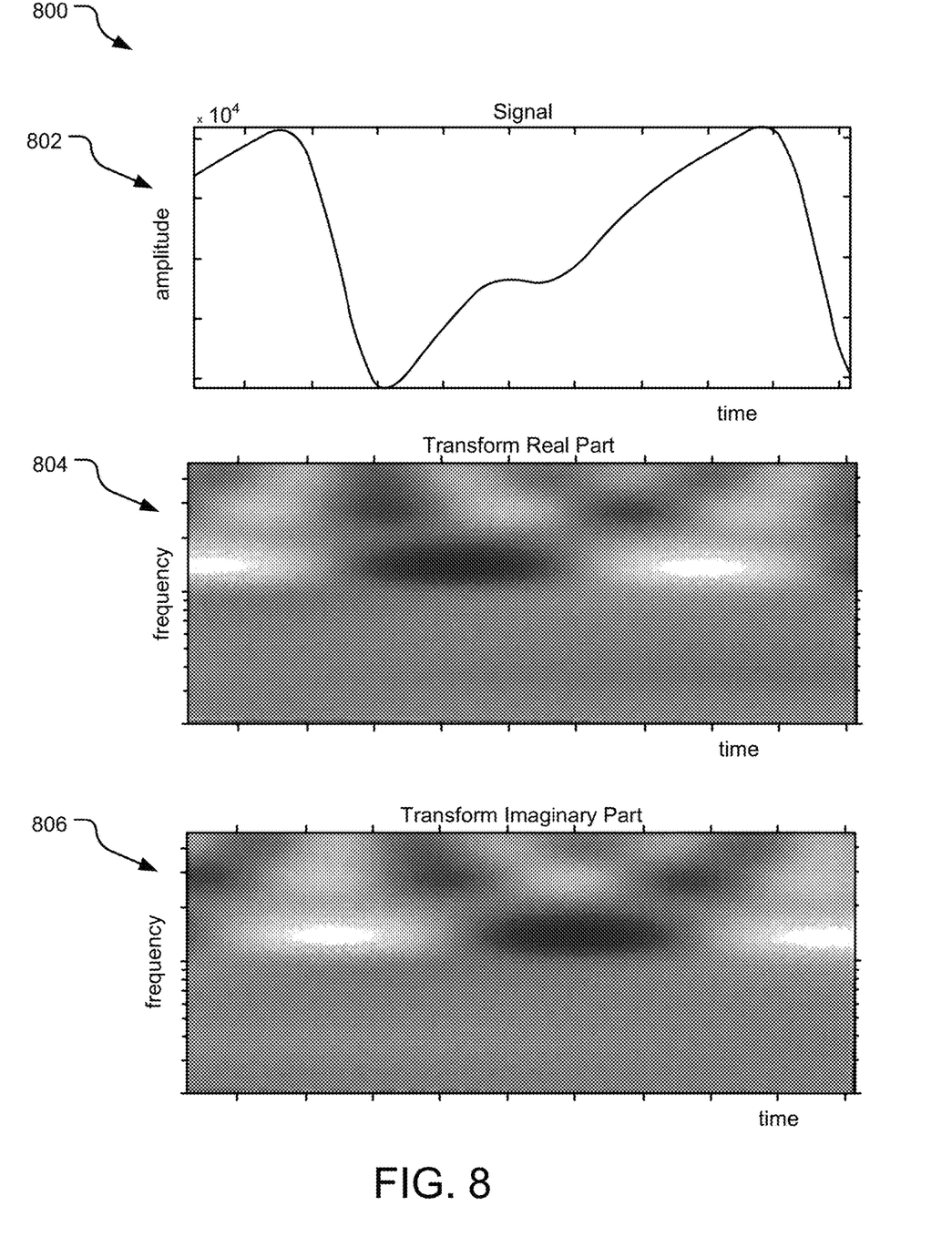
FIG. 8 illustrates example depiction of real and imaginary parts of a transform as generated by the time-frequency transformer disclosed herein.

FIG. 8 illustrates example depiction 800 of real and imaginary parts of a transform as generated by the time-frequency transformer disclosed herein. Specifically, the transform real part 804 and transform imaginary part 806 make up the real and imaginary parts of the complex numbers making up the transform matrix generated by a time-frequency transform of a short segment PPG signal 802. The transform real part 804 and transform imaginary part 806 may be input into the neural network training phase 144a.

Figure 9:
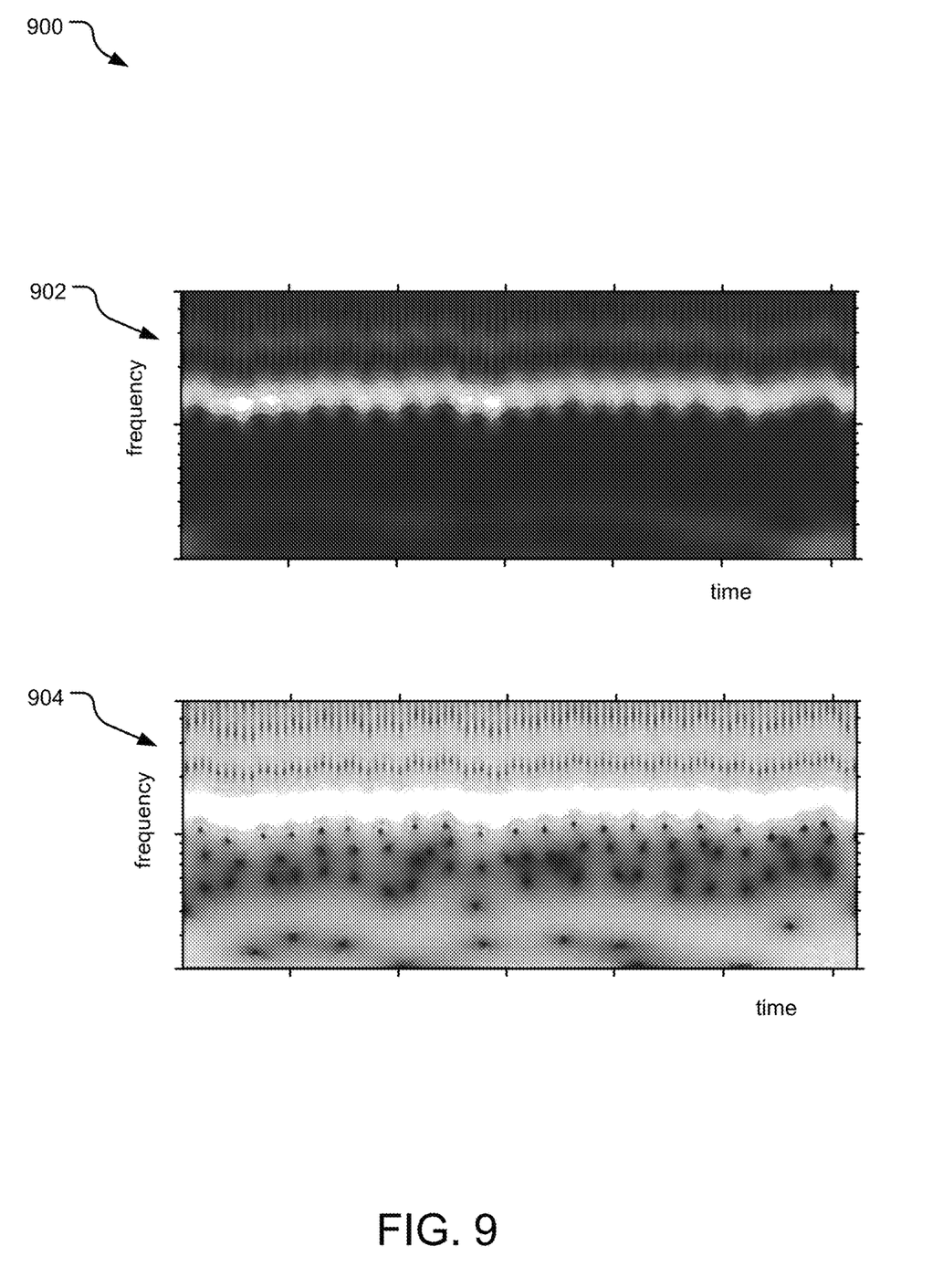
FIG. 9 illustrates example transform modulus that is rescaled logarithmically.

FIG. 9 illustrates time-frequency plots 900 of example transform modulus that is rescaled logarithmically. Specifically, 902 contains an original modulus transform matrix and 904 contains logarithmically scaled modulus generated by rescaling the transform values of the original transform matrix. Such scaling allows smaller features of the original modulus transform matrix to be less dominated by the higher energy features in the signal. Scaling methods other than logarithmic scaling may also be used to scale the transform values in a nonlinear way in order to enhance he subtle features within the signal.

Figure 10:
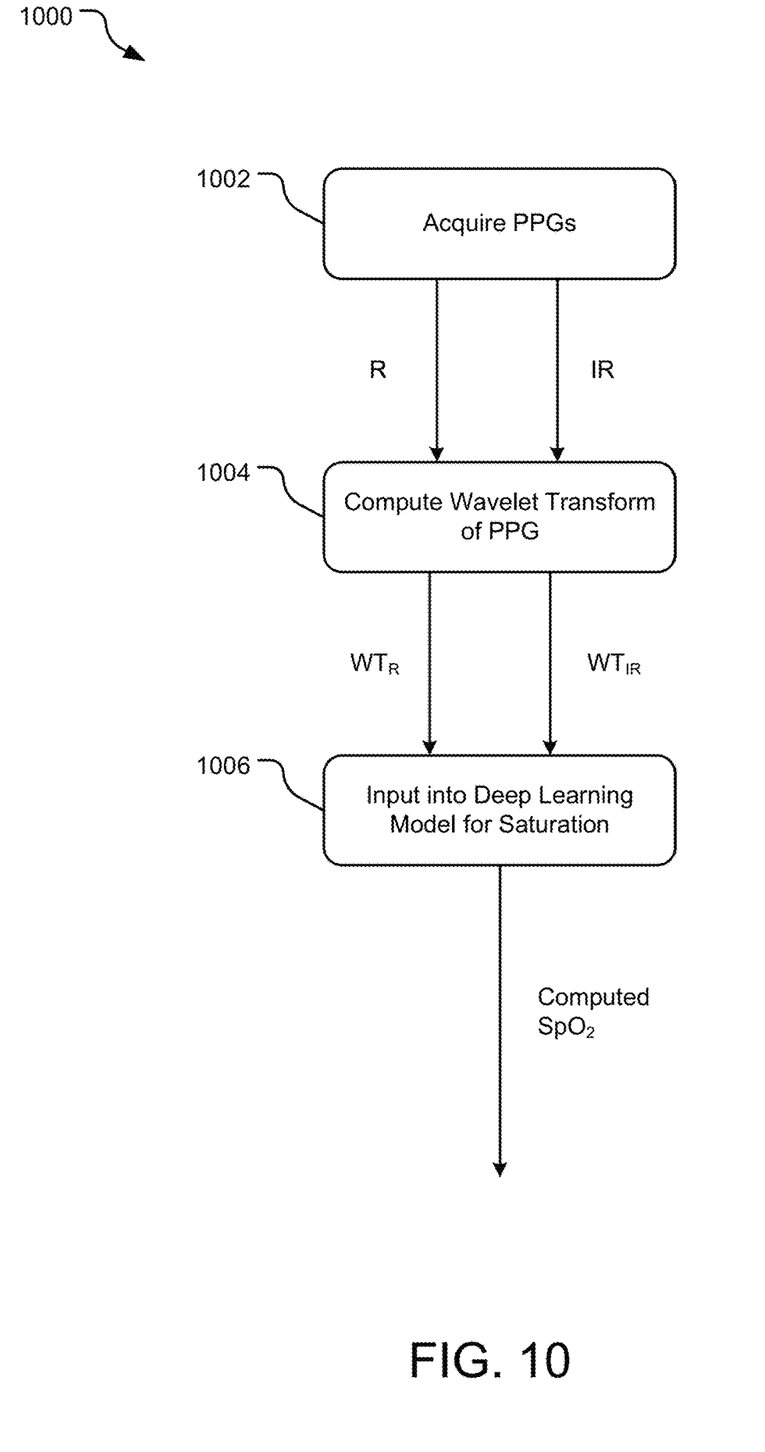
FIG. 10 illustrates example operations of the AI based method of determining oxygen saturation levels disclosed herein.

FIG. 10 illustrates example operations 1000 of the AI based method of determining oxygen saturation levels disclosed herein. An operation 1002 acquires red and infrared PPG signals from an oximeter. An operation 1004 computes wavelet transforms of the input red an infrared PPG signals to generate transform matrices $WT_R$ and $WT_{IR}$. At operation 1006, the transform matrices $WT_R$ and $WT_{IR}$ are input into a deep learning neural network for training the deep learning neural network to generate computed oxygen saturation level or $SpO_2$.

Figure 11:
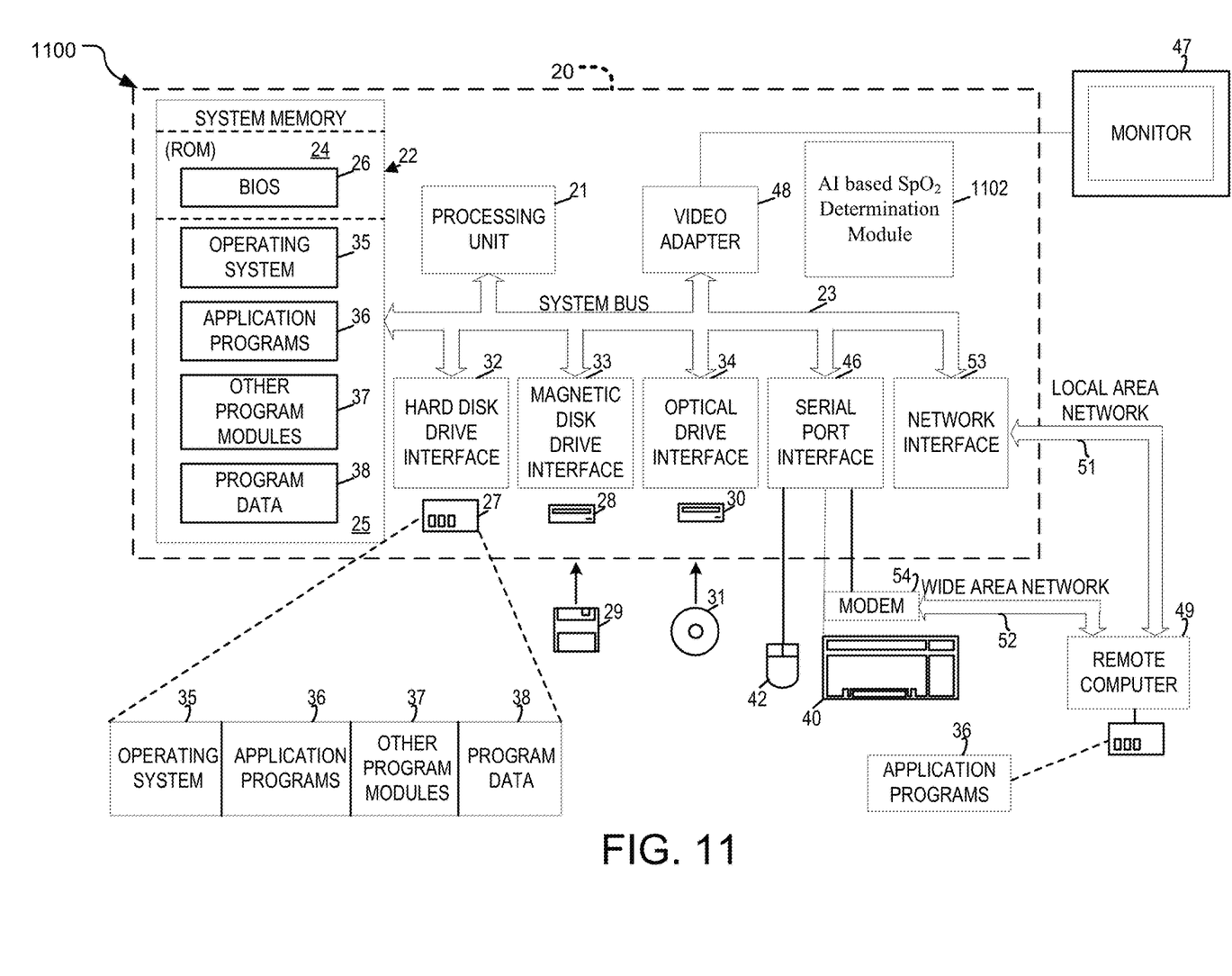
FIG. 11 illustrates an example computing system that may be useful in implementing the described technology.

FIG. 11 illustrates an example system 1100 that may be useful in implementing the described technology for providing attestable and destructible device identity. The example hardware and operating environment of FIG. 11 for implementing the described technology includes a computing device, such as a general-purpose computing device in the form of a computer 20, a mobile telephone, a personal data assistant (PDA), a tablet, smart watch, gaming remote, or other type of computing device. In the implementation of FIG. 11, for example, the computer 20 includes a processing unit 21, a system memory 22, and a system bus 23 that operatively couples various system components including the system memory to the processing unit 21. There may be only one or there may be more than one processing unit 21, such that the processor of the computer 20 comprises a single central-processing unit (CPU), or a plurality of processing units, commonly referred to as a parallel processing environment. The computer 20 may be a conventional computer, a distributed computer, or any other type of computer; the implementations are not so limited.

The system bus 23 may be any of several types of bus structures including a memory bus or memory controller, a peripheral bus, a switched fabric, point-to-point connections, and a local bus using any of a variety of bus architectures. The system memory may also be referred to as simply the memory, and includes read only memory (ROM) 24 and random-access memory (RAM) 25. A basic input/output system (BIOS) 26, containing the basic routines that help to transfer information between elements within the computer 20, such as during start-up, is stored in ROM 24. The computer 20 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated tangible computer-readable media provide non-volatile storage of computer-readable instructions, data structures, program modules and other data for the computer 20. It should be appreciated by those skilled in the art that any type of tangible computer-readable media may be used in the example operating environment.

A number of program modules may be stored on the hard disk drive 27, magnetic disk 28, optical disk 30, ROM 24, or RAM 25, including an operating system 35, one or more application programs 36, other program modules 37, and program data 38. A user may generate reminders on the personal computer 20 through input devices such as a keyboard 40 and pointing device 42. Other input devices (not shown) may include a microphone (e.g., for voice input), a camera (e.g., for a natural user interface (NUI)), a joystick, a game pad, a satellite dish, a scanner, or the like. These and other input devices are often connected to the processing unit 21 through a serial port interface 46 that is coupled to the system bus 23, but may be connected by other interfaces, such as a parallel port, game port, or a universal serial bus (USB) (not shown). A monitor 47 or other type of display device is also connected to the system bus 23 via an interface, such as a video adapter 48. In addition to the monitor, computers typically include other peripheral output devices (not shown), such as speakers and printers.

The computer 20 may operate in a networked environment using logical connections to one or more remote computers, such as remote computer 49. These logical connections are achieved by a communication device coupled to or a part of the computer 20; the implementations are not limited to a particular type of communications device. The remote computer 49 may be another computer, a server, a router, a network PC, a client, a peer device or other common network node, and typically includes many or all of the elements described above relative to the computer 20. The logical connections depicted in FIG. 7 include a local-area network (LAN) 51 and a wide-area network (WAN) 52. Such networking environments are commonplace in office networks, enterprise-wide computer networks, intranets and the Internet, which are all types of networks.

When used in a LAN-networking environment, the computer 20 is connected to the local network 51 through a network interface or adapter 53, which is one type of communications device. When used in a WAN-networking environment, the computer 20 typically includes a modem 54, a network adapter, a type of communications device, or any other type of communications device for establishing communications over the wide area network 52. The modem 54, which may be internal or external, is connected to the system bus 23 via the serial port interface 46. In a networked environment, program engines depicted relative to the personal computer 20, or portions thereof, may be stored in the remote memory storage device. It is appreciated that the network connections shown are examples and other means of communications devices for establishing a communications link between the computers may be used.

In an example implementation, software or firmware instructions for providing attestable and destructible device identity may be stored in memory 22 and/or storage devices 29 or 31 and processed by the processing unit 21. One or more datastores disclosed herein may be stored in memory 22 and/or storage devices 29 or 31 as persistent datastores. For example, an AI based $SpO_2$ determination module 1102 (illustrated within the personal computer 20) may be implemented on the computer 20 (alternatively, the AI based $SpO_2$ determination module 1102 may be implemented on a server or in a cloud environment). The AI based $SpO_2$ determination module 1102 may utilize one of more of the processing unit 21, the memory 22, the system bus 23, and other components of the personal computer 20.

In contrast to tangible computer-readable storage media, intangible computer-readable communication signals may embody computer readable instructions, data structures, program modules or other data resident in a modulated data signal, such as a carrier wave or other signal transport mechanism. The term "modulated data signal" means a signal that has one or more of its characteristics set or changed in such a manner as to encode information in the signal. By way of example, and not limitation, intangible communication signals include wired media such as a wired network or direct-wired connection, and wireless media such as acoustic, RF, infrared and other wireless media.

The implementations described herein are implemented as logical steps in one or more computer systems. The logical operations may be implemented (1) as a sequence of processor-implemented steps executing in one or more computer systems and (2) as interconnected machine or circuit modules within one or more computer systems. The implementation is a matter of choice, dependent on the performance requirements of the computer system being utilized. Accordingly, the logical operations making up the implementations described herein are referred to variously as operations, steps, objects, or modules. Furthermore, it should be understood that logical operations may be performed in any order, unless explicitly claimed otherwise or a specific order is inherently necessitated by the claim language.

The above specification, examples, and data provide a complete description of the structure and use of exemplary embodiments of the invention. Since many implementations of the invention can be made without departing from the spirit and scope of the invention, the invention resides in the claims hereinafter appended. Furthermore, structural features of the different embodiments may be combined in yet another implementation without departing from the recited claims.

What is claimed is:

1. A method, of determining oxygen level saturation, comprising:
    receiving a photoplethysmographic (PPG) signal, the PPG signal including a red PPG signal and an infrared PPG signal;
    generating an input feature matrix by performing time-frequency transform of the PPG signal, wherein generating the input feature matrix further comprises generating a real value vector and an imaginary value vector across a time-frequency plane;
    training a neural network using the input feature matrix, an oxygen saturation level input signal, and the real value vector and the imaginary value vector across a time-frequency plane; and
    generating an oxygen saturation level output signal using the trained neural network.

2. The method of claim 1, wherein generating an input feature matrix by performing time-frequency transform of the PPG signal further comprising generating an input feature matrix by performing a wavelet transform of the PPG signal.

3. The method of claim 2, wherein generating the input feature matrix by performing time-frequency transform of the PPG signal further comprising generating a modulus value vector and a phase value vector across a time-frequency plane.

4. The method of claim 2, wherein generating the input feature matrix by performing a wavelet transform of the PPG signal further comprising generating the input feature matrix by performing a Morlet wavelet transform of the PPG signal.

5. The method of claim 1, further comprising normalizing the PPG signal by a baseline to generate a normalized PPG signal, wherein generating an input feature matrix further comprises generating an input feature matrix by performing time-frequency transform of the normalized PPG signal.

6. The method of claim 1, further comprising rescaling the input feature matrix non-linearly before training a neural network using the input feature matrix.

7. The method of claim 6, wherein rescaling the input feature matrix non-linearly further comprising rescaling the input feature matrix using a logarithmic scaling.

8. The method of claim 1, wherein performing time-frequency transform of the PPG signal further comprising one of performing short time Fourier transform (STFT) of the PPG signal, performing WignerVille transform of the PPG signal, and performing S-transform of the PPG signal.

9. The method of claim 1, further comprising combining two or more vectors of the input feature matrix to generate a combined feature vector and wherein training the neural network further comprising training the neural network with the combined feature vector.

10. In a computing environment, a method performed at least in part on at least one processor, the method comprising:
    receiving a photoplethysmographic (PPG) signal, the PPG signal including a red PPG signal and an infrared PPG signal;
    generating an input feature matrix by performing time-frequency transform of the PPG signal, wherein generating the input feature matrix further comprises generating a real value vector and an imaginary value vector across a time-frequency plane;
    training a neural network using the input feature matrix, an oxygen saturation level input signal, and the real value vector and the imaginary value vector across a time-frequency plane; and
    generating an oxygen saturation level output signal using the trained neural network.

11. The method of claim 10, wherein generating an input feature matrix by performing time-frequency transform of the PPG signal further comprising generating an input feature matrix by performing a wavelet transform of the PPG signal.

12. The method of claim 11, wherein generating the input feature matrix by performing time-frequency transform of the PPG signal further comprising generating a modulus value vector and a phase value vector across a time-frequency plane.

13. The method of claim 11, wherein generating the input feature matrix by performing a wavelet transform of the PPG signal further comprising generating the input feature matrix by performing a Morlet wavelet transform of the PPG signal.

14. The method of claim 10, further comprising rescaling the input feature matrix using a logarithmic scaling before training a neural network using the input feature matrix.

15. The method of claim 14, wherein performing time-frequency transform of the PPG signal further comprising one of performing short time Fourier transform (STFT) of the PPG signal, performing WignerVille transform of the PPG signal, and performing S-transform of the PPG signal.

16. A physical article of manufacture including one or more tangible computer-readable storage media, encoding computer-executable instructions for executing on a computer system a computer process to provide an automated connection to a collaboration event for a computing device, the computer process comprising:
    receiving a photoplethysmographic (PPG) signal, the PPG signal including a red PPG signal and an infrared PPG signal;
    generating an input feature matrix by performing time-frequency transform of the PPG signal, wherein generating the input feature matrix further comprises generating a real value vector and an imaginary value vector across a time-frequency plane; and
    training a neural network using the input feature matrix, an oxygen saturation level input signal, and the real value vector and the imaginary value vector across a time-frequency plane.

17. The physical article of manufacture of claim 16, wherein the computer process further comprising generating an oxygen saturation level output signal using the trained neural network.

18. The physical article of manufacture of claim 17, wherein generating an input feature matrix by performing time-frequency transform of the PPG signal further comprising generating an input feature matrix by performing a wavelet transform of the PPG signal.

19. The physical article of manufacture of claim 18, wherein generating the input feature matrix by performing time-frequency transform of the PPG signal further comprising generating a modulus value vector and a phase value vector across a time-frequency plane.

\* \* \* \* \*